United States Patent
Ng (10) Patent No.: US 9,642,550 B2
(45) Date of Patent: May 9, 2017

(54) CYCLE LENGTH ITERATION FOR THE DETECTION OF ATRIAL ACTIVATIONS FROM ELECTROGRAM RECORDINGS OF ATRIAL FIBRILLATION

(71) Applicant: NORTHWESTERN UNIVERSITY, Evanston, IL (US)

(72) Inventor: Jason Ng, Evanston, IL (US)

(*) Notice: Subject to any disclaimer, the term of this patent is extended or adjusted under 35 U.S.C. 154(b) by 314 days.

(21) Appl. No.: 14/261,031

(22) Filed: Apr. 24, 2014

(65) Prior Publication Data

US 2014/0330148 A1  Nov. 6, 2014

Related U.S. Application Data (60) Provisional application No. 61/819,455, filed on May 3, 2013.

(51) Int. Cl.
*A61B 5/046* (2006.01)
*A61B 5/00* (2006.01)

(52) U.S. Cl.
CPC ............ *A61B 5/046* (2013.01); *A61B 5/7264* (2013.01); *A61B 5/7282* (2013.01)

(58) Field of Classification Search
CPC ...... A61B 5/046; A61B 5/7264; A61B 5/7792
See application file for complete search history.

(56) References Cited

U.S. PATENT DOCUMENTS

| 6,076,014 A * | 6/2000 | Alt ..................... | A61N 1/3962 607/4 |
| 7,668,590 B1 * | 2/2010 | Paris .................... | A61B 5/0245 600/509 |
| 9,031,649 B2 * | 5/2015 | Ousdigian ........... | A61B 5/0464 607/14 |

OTHER PUBLICATIONS

J Ng, JJ Goldberger, "Understanding & Interpreting Dominant Frequency Analysis of AF Electrograms: Frequency Domain Analyses of Atrial Fibrillation Recordings", J Cardiovasc Electrophysiol. 2007;18(6):680-685.

GS Tewolde, C Wu, Y Wang, W Sheng, "Distributed Multi-Robot Work Load Partition in Manufacturing Automation", 4th IEEE conference on Automation Science and Engineering Aug. 23-26, 2008.

Ciaccio EJ, Biviano AB, Whang W, Wit AL, Garan H, Coromilas J, "New methods for estimating local electrical activation rate during atrial fibrillation", Heart Rhythm Jan. 2009;6(1):21-32.

Berenfeld O, Ennis S, Hwang E, Hooven B, Grzeda K, Mironov S, Yamazaki M, Kalifa J, Jalife J, "Time- and frequency-domain analyses of atrial fibrillation activation rate: the optical mapping reference", Heart Rhythm Nov. 2011;8(11):1758-65.

* cited by examiner

*Primary Examiner* — Mark W Bockelman
(74) *Attorney, Agent, or Firm* — Klintworth & Rozenblat IP LLC (57) ABSTRACT

A method is provided of analyzing a cardiac electrogram using a computer. In one step, a determination is made as to a plurality of cycle lengths between a plurality of activation peaks of the cardiac electrogram. In another step, a determination is made as to whether a mean of the plurality of cycle lengths meets at least one criteria. The method may be used to iteratively adjust a detection threshold level for detecting atrial fibrillation based on the cardiac electrogram.

11 Claims, 8 Drawing Sheets

CYCLE LENGTH ITERATION FOR THE DETECTION OF ATRIAL ACTIVATIONS FROM ELECTROGRAM RECORDINGS OF ATRIAL FIBRILLATION

RELATED APPLICATIONS

The disclosure is a utility patent application claiming priority to and the benefit of U.S. provisional patent application Ser. No. 61/819,455, entitled Cycle Length Iteration for the Detection of Atrial Activations from Electrogram Recordings of Atrial Fibrillation, filed on May 3, 2013, which is hereby incorporated by reference in its entirety.

FIELD OF THE DISCLOSURE

This disclosure relates generally to systems and methods of identifying atrial fibrillation, and more particularly, to a system of identifying sites with fast activation rates that could be ablation targets.

BACKGROUND OF THE DISCLOSURE

Approximately 2.2 million Americans and 4.5 million Europeans have atrial fibrillation, and this infirmity is expected to increase proportionally with an aging population. Between 1990 to 2005, out of 270,000 inpatient records showing a diagnosis of atrial fibrillation from the National Hospital Discharge Survey, there were 1,144 individuals who were treated with contact ablation, with an increasing percentage of treatment towards 2005. Assuming the 1990-2005 trend is maintained, this would suggest that roughly 2.0% of the hospitalized atrial fibrillation sufferers would be treated via atrial ablation by 2015. Further assuming that 10% of current atrial fibrillation sufferers in the US are hospitalized by 2015, this suggests that ~4,400 individuals will be treated with atrial ablation within this time period.

Diagnosed atrial fibrillation is simplistically categorized as a function of the duration and frequency of atrial fibrillation episodes. Generally, atrial fibrillation episodes that persist for <30 s are not categorized. If there is but one (i.e., a first) diagnosed episode of atrial fibrillation, the atrial fibrillation is categorized as "first detected atrial fibrillation." If subsequent episode of atrial fibrillation occur each with durations <7 days, the condition generally is termed "paroxysmal atrial fibrillation." Episodes that recur with durations >7 days generally are termed "persistent atrial fibrillation." The atrial fibrillation condition that is characterized by long term ongoing episodes of atrial fibrillation is generally termed "permanent atrial fibrillation."

Contact atrial electrograms recorded during atrial fibrillation (AF) are characterized by rapid deflections with changing amplitudes, cycle lengths (CLs), and morphologies. Unlike other atrial tachyarrhythmias with regular activation patterns, atrial fibrillation has complex activation patterns that make elucidation of atrial fibrillation mechanisms difficult. Mapping of atrial cycle length or atrial activation rates has been proposed in the art as an alternative to mapping activation sequences.

It has been hypothesized that sites with the fastest activation rates represent the locations of the drivers of atrial fibrillation (focal or reentrant) and could be potential ablation targets. Some support for this contention has been found in both, clinical and experimental studies. The measurements of atrial fibrillation activations rates can also be used to track drug effects, autonomic manipulations, and ablation response.

One of the principal limitations of the activation rate mapping approach is the technical difficulty encountered in obtaining reliable measurements. The complexity of atrial fibrillation electrograms renders detection of deflections and the calculation of the cycle lengths and activation rates difficult in both, the time and the frequency domains. Deflection-to-deflection intervals can be measured manually with the use of calipers, but because of the variability of atrial fibrillation cycle lengths, an average of several intervals is needed to characterize the atrial fibrillation cycle length. This is an arduous task for the technician making the measurements.

An alternative method that has been employed in the art is a manual setting of an amplitude or slope threshold value that can be used to detect deflections. The principal limitation of this manual threshold approach is the subjectivity required on the part of the technician to distinguish noise from atrial activation. In addition, automatic algorithms that detect deflections based on fixed threshold levels are prone to oversensing or undersensing.

Dominant frequency (DF) analysis is yet another known approach, and uses the frequency that contains the most power as the estimate of the activation rate. Dominant frequency analysis works well in the estimation of activation rates if the atrial fibrillation electrograms have a certain amount of regularity, but the correlation is reduced with highly irregular waveforms and complex morphologies. Such irregularity of the waveforms and signal complexity renders dominant frequency analysis inaccurate.

There is a need for a robust algorithm that produces accurate results that can be validated and withstand rigorous testing. There is also a need for a system that produces a more accurate and robust methodology of locating optimal sites for ablation in patients suffering from atrial fibrillations.

SUMMARY OF THE DISCLOSURE

The foregoing and other objects are achieved by this disclosure, which provides a new algorithm that uses cycle length iteration (CLI) to detect atrial complexes. The algorithm operates on the assumption that atrial fibrillation cycle lengths have distributions where mean and median cycle lengths are approximately equal. Using manually marked electrograms as the standard, the accuracy of the cycle length iteration algorithm is evaluated to detect activations and to compute atrial fibrillation cycle lengths. The results then are compared against fixed threshold algorithms and the results of a dominant frequency analysis.

The present new algorithm for the detection of activations and the calculation of activation rates in atrial fibrillation electrograms is termed the "Cycle Length Iteration" (CLI) technique. When evaluated in a set of 503 10-second electrogram signals with a total of 29,506 manually marked activations, detection of activations with cycle length iteration has been found to have low undersensing and oversensing rates of 2.4% and 4.6%, respectively. In comparison, the more commonly used fixed threshold technique is characterized with undersensing and oversensing rates of 4.1% and 5.3%, respectively. The inventive cycle length iteration algorithm has achieved measured mean atrial fibrillation cycle lengths that on average are within $7.9 \pm 9.6$ ms of the manually measured mean cycle lengths. In comparison, mean cycle lengths from an automatic fixed threshold algorithm were on average within $11.5 \pm 15.1$ ms of the manually measured mean cycle lengths. Mean cycle lengths derived from dominant frequency analysis were within 12.7±13.8 ms of the manually measured mean cycle lengths.

The challenge of dealing with atrial fibrillation signals is that the variation of amplitudes and morphologies of the deflections can make it difficult to distinguish activation from noise. Thus, in the specific illustrative embodiment of the disclosure herein described, there is no localized noise suppression performed in this algorithm.

Accurate detection of atrial fibrillation activation and calculation atrial fibrillation cycle length is possible with the present cycle length iteration algorithm. In addition to such accuracy, cycle length iteration is sufficiently efficient computationally that it can be implemented in a real-time calculation environment. Moreover, the cycle length iteration algorithm is a useful feature in cardiac mapping systems that are used in atrial fibrillation ablation procedures.

Thus, some of the potential uses of various embodiments of the present disclosure include:

Locating atrial fibrillation drivers;
Creating atrial fibrillation activation maps/movies; and
Tracking effects of drugs/ablation during ablation procedure.

It is to be understood, however, that the potential applications of a system that achieves the objectives sought to be achieved by the present disclosure are not limited as related to arrhythmias diagnosis with an interest in detecting ablation targets. Additionally, the present disclosure can be employed a part of a medical device as either a software suite or embedded in a diagnostic device. In the context of a diagnostic device, the algorithm of the present disclosure is a feature of a cardiac mapping system that can be selected on an on-screen menu.

In one embodiment of the disclosure a method is disclosed of analyzing a cardiac electrogram using a computer. In one step, a determination is made as to a plurality of cycle lengths between a plurality of activation peaks of the cardiac electrogram. In another step, a determination is made as to whether a mean of the plurality of cycle lengths meets at least one criteria.

In another embodiment of the disclosure a system is disclosed for analyzing a cardiac electrogram. The system includes an electrogram device, a processor, and a memory. The electrogram device is configured to take, deliver, or store a cardiac electrogram. The processor is in electronic communication with the electrogram device. The memory is in electronic communication with the processor. The memory includes programming code for execution by the processor. The programming code is configured to: determine a plurality of cycle lengths between a plurality of activation peaks of the cardiac electrogram; and determine whether a mean of the plurality of the cycle lengths meets at least one criteria.

In still another embodiment of the disclosure a non-transitory computer readable medium is disclosed. The non-transitory computer readable medium is configured to, using a processor, analyze a cardiac electrogram. The non-transitory computer readable medium includes programming code to command the processor to: determine a plurality of cycle lengths between a plurality of activation peaks of the cardiac electrogram, and determine whether a mean of the plurality of the cycle lengths meets at least one criteria.

BRIEF DESCRIPTION OF THE DRAWINGS

Comprehension of the disclosure is facilitated by reading the following detailed description, in conjunction with the annexed drawing, in which:

FIGS. 2(a), 2(b), and 2(c) are graphical illustrations of the cycle length iteration method, specifically.

FIGS. 3(a), 3(b), 3(c), 3(d), and 3(e) are graphical illustrations that illustrate the evaluation of the cycle length iteration algorithm against the manual markings from markers A and B and the intersection of the markings of A and B (A B) for different segment lengths, specifically

FIGS. 4(a), 4(b), and 4(c) are graphical representations, wherein

FIGS. 5(a) and 5(b) are graphical representations wherein

DETAILED DESCRIPTION OF THE DISCLOSURE

Atrial fibrillation (AF) bipolar electrograms are characterized by varying morphology, amplitude, and cycle lengths (CLs). In one embodiment of the disclosure an atrial fibrillation electrogram detection algorithm iteratively adjusts the detection threshold level until the mean cycle length converges with the median cycle length. Stated differently, the algorithm identifies the minimum peak value using cycle length iteration. The mean cycle length is the average time between successive activations (peaks). The median cycle length is the time between successive activation that ranks at the 50th percentile of all times between successive activations.

Absence of discrete p waves is the criterion for diagnosing atrial fibrillation from the surface electrocardiogram. However, the disclosure has been applied to electrograms recording made in contact with the atria, where discrete activations can still be detected although they are much more rapid than a normal rhythm.

Using a protocol approved by the Office for the Protection of Research Subjects Institutional Review Board of Northwestern University, an experiment was conducted in which 291 atrial fibrillation electrograms were recorded from 13 patients, 11 of whom were males, in the range of 58±10 years of age. The patients all were suffering from atrial fibrillation and had not yet undergone radio frequency ablation. Four patients had paroxysmal atrial fibrillation and nine had persistent atrial fibrillation. Mapping and recording were performed using a Navi-Star catheter (Biosense Webster, Inc., Diamond Bar, Calif.). For each patient, bipolar electrograms were sequentially obtained from at least 10 sites in the right atrium and at least 10 sites in the left atrium and stored on the Prucka CardioLab EP System (GE Healthcare, Waukesha, Wis.). The electrograms were sampled at a rate of 977 Hz and filtered with a 30 Hz high pass filter. High pass and low pass filtering was performed on the entire electrogram signal. Signals from a coronary sinus catheter were also recorded simultaneously for each recording made by the Navi-star catheter. During atrial fibrillation one can expect 4 to 9 activations per second for the duration of the recording.

All electrogram analyses were performed offline on a computer using tools developed in MATLAB (Mathworks, Natick, Mass.). In one embodiment of the disclosure, Matlab is used simply to calculate the sum of the cycle lengths divided by the number of cycles. The standard definition of median (50th percentile) is used. Differentiation is used in some embodiments of the disclosure to calculate the cycle lengths from the times of the detected peaks. The differentiation step accomplishes the same thing as high pass filtering, which is to accentuate sharp deflections and attenuate slower changes in the signal. Matlab is the programming language that was used to implement the specific illustrative embodiment of the algorithm. In the tested embodiment of the disclosure, there was no existing program that was modified for the present implementation.

Manual markings by two independent operators were performed and the intersection between the two sets of marking was used to compare the cycle length iteration (CLI) algorithm with fixed threshold and dominant frequency (DF) for the estimation of cycle length using segment lengths ranging from 2 to 16 seconds. The operators were instructed to mark each activation at the point of highest absolute amplitude. For electrograms with discrete but fractionated activation complexes with clear isoelectric periods before and after the complex, the highest amplitude deflection was chosen. No markings were made within 50 ms of a previous mark. In addition to the two independent sets of markings, the cycle length iteration algorithm used the intersection of the two sets of manual marking. The intersection was defined as the marks that are common to both sets of manual markings within 50 ms.

The sensing rates of the cycle length iteration algorithm improved with increasing segment lengths. At segment lengths of 10 s, the sensing rates stabilized with undersensing, oversensing, and total discrepancy rates of 2.4%, 4.6% and 7.0%, respectively, and with absolute differences in mean and median cycle lengths compared to manual markings of 7.9±9.6 ms and 5.6±6.8 ms, respectively. The cycle length iteration algorithm had lower discrepancy rates and cycle length differences than the dominant frequency and fixed threshold-based measurements of cycle length for all segment lengths. It is to be noted that the algorithm of the present disclosure detects activations from only a single electrogram recording at a time. However, testing of the algorithm was performed on multiple electrograms. The 10 s segment length appears to be when the performance of the algorithm appears to stabilize. However, because the algorithm requires estimates of mean and median cycle length, the longest possible segment length is desirable. It is also expected that the optimal segment length will vary from patient-to-patient. Additionally, the optimal segment length can vary depending on the nature of the atrial fibrillation from which the patient suffers. For example, persistent and permanent atrial fibrillation tends to have faster and more complex electrograms compared to those of paroxysmal or first detected atrial fibrillation. Thus, the disclosure is not limited to a 10 s segment length.

It is seen from the foregoing experimental results that the cycle length iteration algorithm enables accurate detection of atrial fibrillation activations that more closely approximate manual marking than dominant frequency or fixed threshold algorithms. The robust method of the present disclosure can be used for cycle length measurements in either real-time and offline settings, as well as in the mapping of atrial fibrillation.

Figure 1:
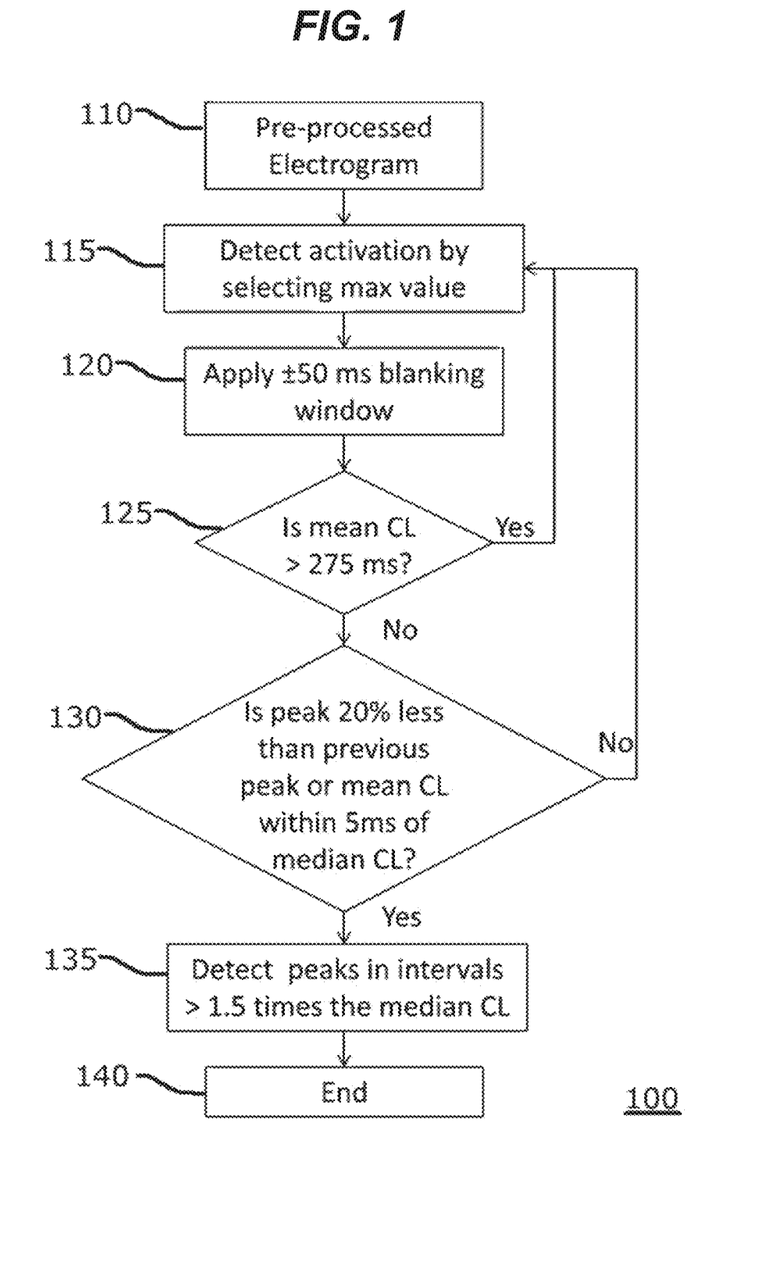
FIG. 1 is a simplified flow chart representation that is useful in describing the steps of the cycle length iteration (CLI) algorithm.

The iterative process for detecting the activations is summarized in the flow chart of FIG. 1, which is a simplified flow chart representation that is useful in describing the steps of the cycle length iteration (CLI) algorithm. The flow chart of FIG. 1 may be used to adjust a detection threshold level for detecting atrial fibrillation based on a cardiac electrogram. As shown in this figure, a pre-processed electrogram is provided at function block 110. The pre-processing of the electrogram includes the following steps:

1) 40 Hz high pass filtering ($2^{nd}$ order Butterworth filter);
2) rectification; and
3) 30 Hz low pass filtering ($2^{nd}$ order Butterworth filter).

In the practice of one embodiment of the disclosure, the electrograms are stored as discrete amplitude values (voltages) for every time point. In one embodiment, one amplitude is acquired at approximately every 1 millisecond. The cycle lengths are calculated once the peaks of the filtered electrograms are detected.

At function block 115, the waveform peak having the highest magnitude is the first detected activation time. Next, at function block 120, all peaks occurring within a ±50 ms blanking period (window), i.e., before and after the detected beat, are removed/excluded. A determination is made at function block 125 as to whether the mean cycle length (CL) is greater than 275 ms. If it is, then the next largest peak is detected at function block 115, and is added to the set. Then, the blanking period of function block 120 is applied again. The process of detecting the next peak and applying the blanking period is repeated until the mean cycle length is less than 275 ms and one of the following two conditions are met at function block 130:

1) the mean cycle length is within 5 ms of the median cycle length, or
2) the magnitude of an amplitude of the current peak is at least 20% less than the magnitude of the amplitude of the previously detected peak.

The values for 275 ms, 5 ms, and 20% were somewhat arbitrarily determined and can be adjusted in the practice of some embodiments of the disclosure. However, increasing the range too much will likely lead to undersensing.

If the conditions are not met, then the process reverts to function block 115 where the waveform peak having the highest magnitude is again detected and the process repeated. However, if the conditions are met, then the algorithm proceeds to a final postprocessing step at function block 135 that involves finding cycle lengths greater than 1.5 times the median cycle length. A cycle length >1.5 times the median cycle length would represent a fairly large gap in the electrogram signal where a peak was not detected. This step would search within this gap to see if there were any low amplitude peaks that might have been missed. The largest peak, if present, within the interval and not within 50 ms of another peak is included in the set of activations. This process is repeated until there are no more cycle lengths (i.e. intervals) greater than 1.5 times the median cycle length with peaks between them, whereupon the process ends at function block 140. In other embodiments, the steps of the method of FIG. 1 may vary in substance or in order, one or more steps may be not followed, or one or more additional steps may be added.

In the event that the algorithm herein described is applied to a cardiac electrogram that is not characterized with atrial fibrillation, the present embodiment of the algorithm will continue to find peaks that do not represent activations (e.g., noise).

It is to be noted that the 275 ms cycle length limitation was determined empirically. Thus, the disclosure is not limited to this cycle length. In addition, there are variations in cycle length between patients and type of atrial fibrillation. Although the 275 ms cycle length limitation was fixed for the evaluation of the algorithm, it is to be user-adjustable in the practice of some embodiments of the disclosure. Atrial fibrillation cycle lengths are generally <250 ms.

Figure 1A:
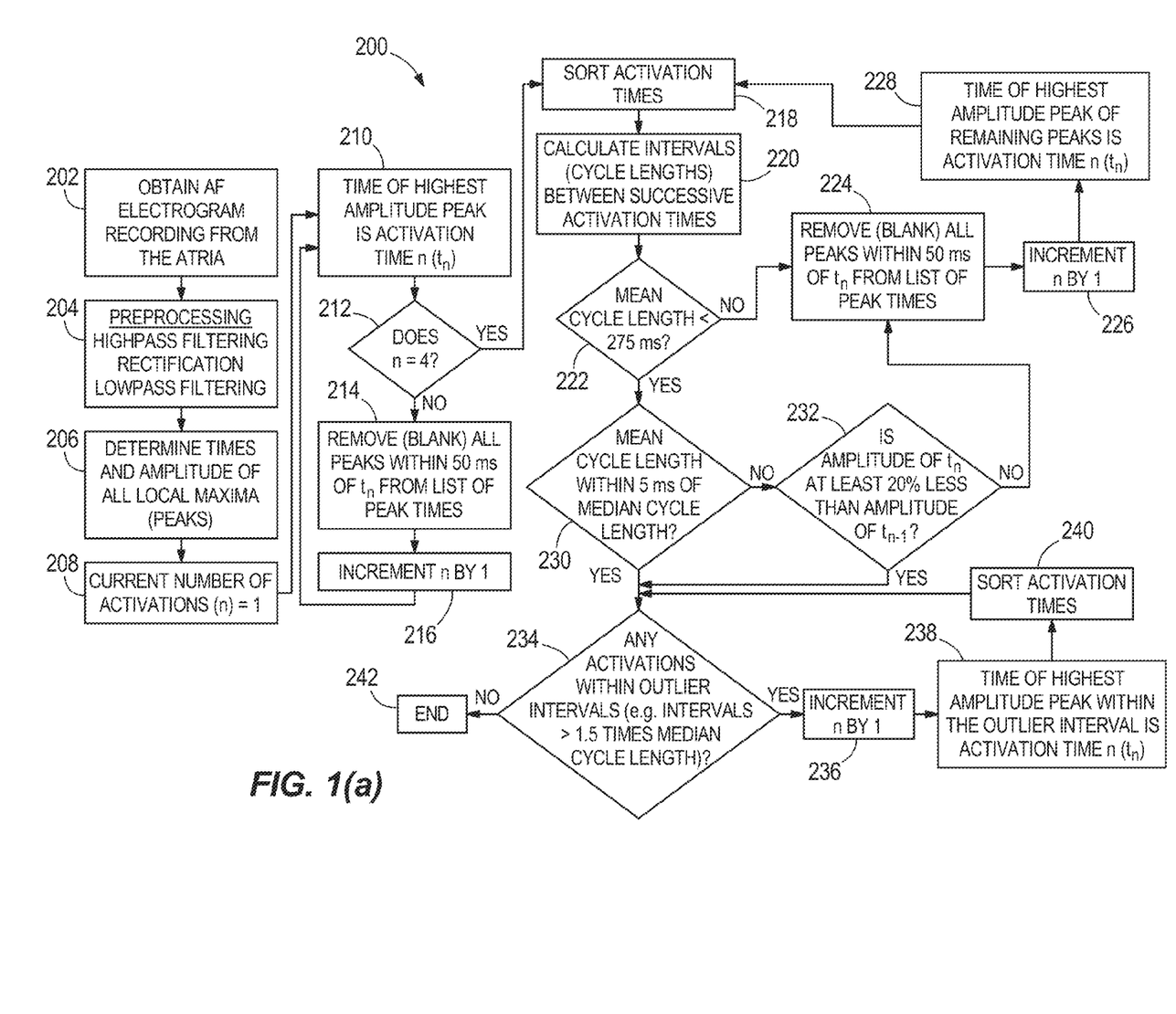
FIG. 1(a) is a flow chart illustrating one embodiment of a method for analyzing cardiac electrograms using a computer.

FIG. 1(*a*) is a flow chart illustrating one embodiment of a method 200 for analyzing cardiac electrograms using a computer. The method 200 may be used to adjust a detection threshold level for detecting atrial fibrillation based on the cardiac electrogram. In step 202, an electrogram is obtained. The method then proceeds to step 204. In step 204, the electrogram is preprocessed using filtering and rectification. The filtering may comprise highpass or lowpass filtering. The method then proceeds to step 206. In step 206, times and amplitudes of all peaks of the electrogram are determined. The method then proceeds to step 208. In step 208, the current number of activations is set to n=1. The method then proceeds to step 210. In step 210, the time of the highest activation peak is determined to be $tn=t_1$. The method then proceeds to step 212. In step 212, a determination is made as to whether n=4. If n does not equal 4 then the method proceeds to step 214.

In step 214 all peaks within 50 ms of $t_n$ are removed/blanked/excluded. The method then proceeds to step 216. In step 216 n is incremented by 1. The method then proceeds to step 210 and repeats the process from step 210. However, if in step 212 a determination is made that n=4 then the method proceeds to step 218. In step 218 the activation times detected in step 206 are sorted chronologically. The method then proceeds to step 220. In step 220 the cycle lengths (intervals) between successive activation times are calculated. The method then proceeds to step 222. In step 222 a determination is made as to whether the mean cycle length is less than 275 ms using the cycle lengths determined in step 220. If a determination is made in step 222 that the mean cycle length is not less than 275 ms then the method proceeds to step 224.

In step 224 all peaks within 50 ms of $t_n$ using the list of peak times are removed/blanked/excluded. The method then proceeds to step 226. In step 226 n is incremented by 1. The method then proceeds to step 228. In step 228 the time of the highest amplitude peak of the remaining peaks is determined for activation time n to be $t_n$. The method then proceeds to step 218 and repeats the process from step 218. If in step 222 a determination is made that the mean cycle length is less than 275 ms then the method proceeds to step 230.

In step 230 a determination is made as to whether the mean cycle length is within 5 ms of the median cycle length. If in step 230 a determination is made that the mean cycle length is not within 5 ms of the median cycle length then the method proceeds to step 232. In step 232 a determination is made as to whether the amplitude of $t_n$ is at least 20% less than the amplitude of $t_{n-1}$. If in step 232 a determination is made that the amplitude of $t_n$ is not at least 20% less than the amplitude of $t_{n-1}$ then the method proceeds to step 224 and repeats the process from step 224. If in step 232 a determination is made that the amplitude of $t_n$ is at least 20% less than the amplitude of $t_{n-1}$ then the method proceeds to step 234. Also, if in step 230 a determination is made that the mean cycle length is within 5 ms of the median cycle length then the method proceeds to step 234.

In step 234 a determination is made as to whether any cycle lengths (intervals) are greater than 1.5 times the median cycle length. If in step 234 a determination is made that there are one or more cycle lengths that are greater than 1.5 times the median cycle length then the method proceeds to step 236. In step 236 n is incremented by 1. The method then proceeds to step 238. In step 238 the time of the highest amplitude peak within the cycle lengths which are greater than 1.5 times the median cycle length is set as activation time n as $t_n$. The method then proceeds to step 240. In step 240 the activation times are sorted. The method then proceeds to step 234 and repeats the process from step 234. If in step 234 a determination is made that there are not any cycle lengths that are greater than 1.5 times the median cycle length then the method proceeds to step 242 and ends the process. In other embodiments, the steps of the method of FIG. 1(*a*) may vary in substance or in order, one or more steps may be not followed, or one or more additional steps may be added.

In the embodiment of FIG. 1(*a*) the method 200 iteratively adjusts a detection threshold level for detecting atrial fibrillation based on the cardiac electrogram until the following criteria are met: the mean of the plurality of the cycle lengths is less than a predetermined time; the mean of the plurality of the cycle lengths is within a first predetermined range of a median of the plurality of the cycle lengths, or an amplitude of one of the plurality of the activation peaks is outside a second predetermined range of the amplitude of a preceding activation peak; and none of the plurality of the cycle lengths are outside a third predetermined range of a median of the plurality of the cycle lengths. In other embodiments, the required criteria can comprise any combination of the above criteria, or in still other embodiments the number and substance of the criteria may vary further.

Figure 1B:
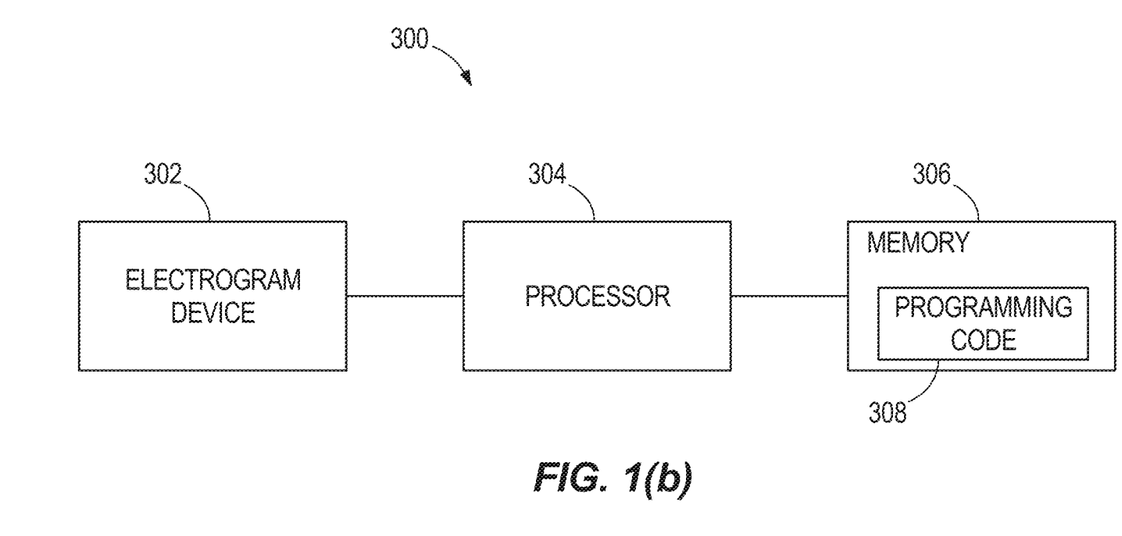
FIG. 1(b) illustrates one embodiment of a system for analyzing a cardiac electrogram.

FIG. 1(*b*) illustrates one embodiment of a system 300 for analyzing a cardiac electrogram. The system 300 may follow the method of FIG. 1 or 1(*a*). The system 300 may comprise an electrogram device 302, a processor 304, and a memory 306 (also referred to herein as a non-transitory computer readable medium) containing programming code 308 for execution by the processor 304. The electrogram device 302 may be configured to take, deliver, or store a cardiac electrogram. The processor 304 is in electronic communication with the electrogram device 302. The memory 306 is in electronic communication with the processor 304. The programming code 308 may be configured to follow the method of FIG. 1 or 1(*a*). In other embodiments, the programming code 308 may be configured to follow varying methods. In still other embodiments, the system 300 may vary.

Figure 2:
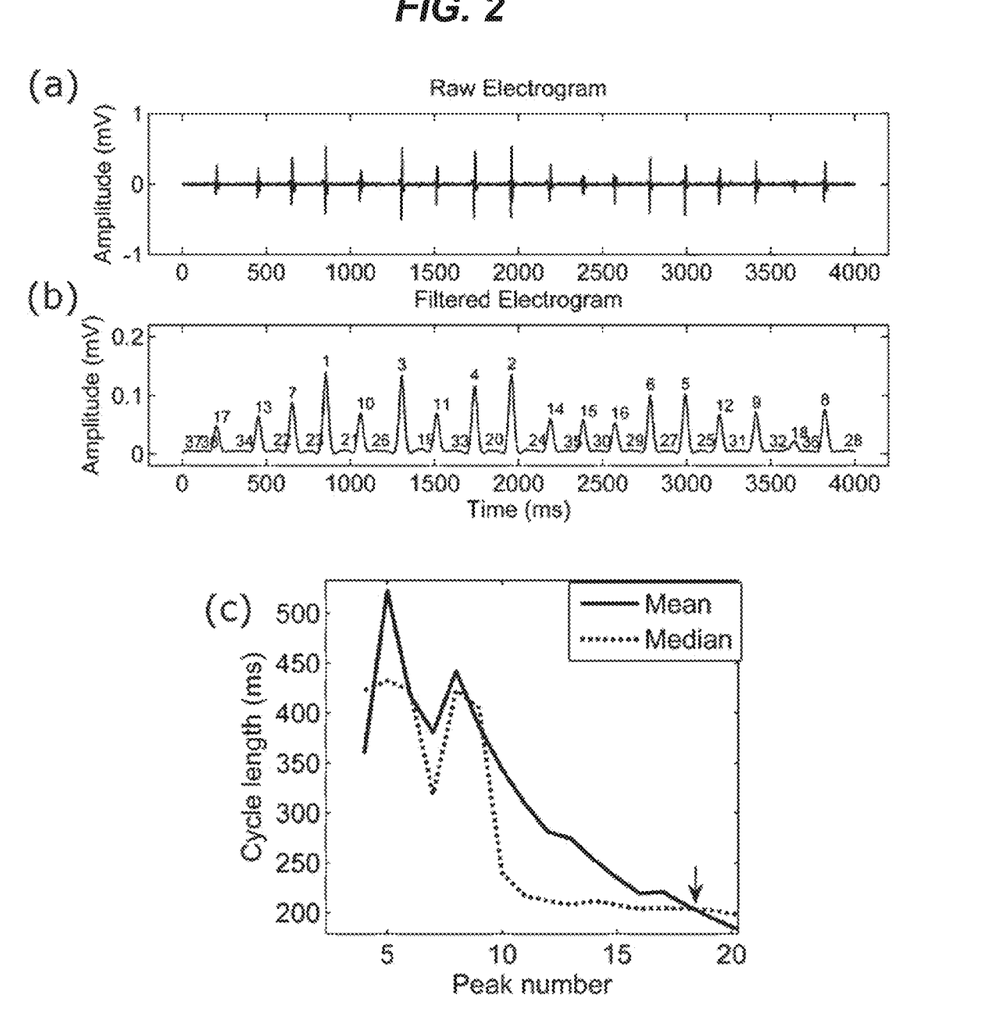
FIG. 2(a) depicts raw unfiltered electrograms.
FIG. 2(b) depicts electrograms after rectification and low pass filtering with peaks ranked based on amplitude.
FIG. 2(c) depicts mean and median cycle length calculation after adding peaks one by one, the mean and median cycle lengths converging after 18 peaks.

FIGS. 2(*a*), 2(*b*), and 2(*c*) are graphical illustrations of the cycle length iteration method. FIG. 2(*a*) depicts raw unfiltered electrograms, FIG. 2(b) depicts electrograms after rectification and low pass filtering with peaks ranked based on amplitude, and FIG. 2(c) depicts mean and median cycle length calculation after adding peaks one by one, the mean and median cycle lengths converging after 18 peaks. More specifically, FIG. 2 shows an example of the mean/median cycle length convergence when the 18th activation is added to the set.

Unlike other methods of detecting optimal sites for ablation proposed in the art, the method of the present disclosure is applicable to complex arrhythmias. Compared to manual measurements, the inventive method requires significantly less effort and time. In general, atrial ablation, compared to medicinal therapy, has been shown to lead to a higher quality of life than medicinal therapy and is price competitive within a 4-8 year period.

Evaluation of the Cycle Length Iteration Algorithm

The cycle length iteration algorithm was evaluated on contiguous atrial fibrillation segments of each of the following segment lengths: 2, 4, 6, 8, 10, 12, 14, and 16 s. Detected activation by the cycle length iteration algorithm that is within ~75 ms of a manually marked activation were considered matched activations. Detected activations not within ~75 ms of a manually marked activation that had not already been classified as a matched activation were considered oversensed activations. A manually marked activation that was not within ~75 ms of a detected activation were considered undersensed activations. Oversensing and undersensing rates were calculated as percentages of the total number of marked activations. Agreement in cycle length was measured by calculating the absolute difference between the mean/median cycle length of each segment between the manual and cycle length iteration algorithm.

Comparison with other Cycle Length Estimation Methods

Agreement of the cycle length iteration algorithm with the manually marked activations was compared against the following: 1) activations detected using an optimum fixed detection threshold and 2) cycle length calculated from dominant frequency.

Fixed threshold detection was performed using the filtered and rectified signal to detect the activations. With this approach, all peaks (taking into account the 50 ms blanking period) above a giving threshold value were considered activations. A range of threshold values were tested to determine the optimal threshold value. Thresholds based on raw amplitude (in μVs) were tested in a 1 to 50 μV range with 1 μV increments. Thresholds based on the percentage of the maximum amplitude were tested in a 0.5 to 25% range with 0.5% increments. Thresholds based on the percentage of one standard deviation were tested in a 2 to 100% range with 2% increments. For each type and segment duration, the thresholds producing the minimum combined oversensing and undersensing rates were considered the optimum thresholds.

Dominant frequencies in this study were calculated as previously described. First, the electrogram segments were bandpass filtered with cutoff frequencies of 40 and 250 Hz using a second-ordered Butterworth filter. The filtered signals were then rectified and lowpass filtered at 20 Hz also using a second-ordered Butterworth filter. The power spectrum was then calculated using the Fast Fourier Transform. The dominant frequency was defined as the frequency that contained the highest power in the 3 to 20 Hz band. The atrial fibrillation cycle length from dominant frequency (DF CL) was calculated as 1000/DF. As dominant frequency estimates activation rate without the detection of activations, only the absolute difference between dominant frequency cycle length and manual cycle length was evaluated for each segment duration Absolute differences in cycle length measurements and manually marked cycle lengths of the multiple methods were compared using the known Wilcoxon signed rank test. P values less than 0.05 were considered statistically significant.

Results

In total 291 electrogram recordings were obtained. Twenty-seven electrograms where the atrial activations could not easily be distinguished from the noise were excluded. The remaining set of electrograms were obtained from a total of 123 right atrial sites and 141 left atrial sites with an average duration of 27.5±9.0 s. The average mean and median cycle lengths were 159.9±24.9 ms and 161.0±24.9 ms, respectively. It is to be noted that Table 1 shows the number of segments obtained from the 291 electrogram recordings that were used for the testing of the present algorithm. The number of contiguous segments analyzed for each segment duration are summarized in the table.

TABLE 1

NUMBER OF SEGMENTS AND ACTIVATIONS ANALYZED FOR EACH SEGMENT LENGTH STUDIED

| Segment Length | Number of Segments | Number of Activations |
| --- | --- | --- |
| 2 s | 3419 | 38610 |
| 4 s | 1653 | 37808 |
| 6 s | 1036 | 36133 |
| 8 s | 736 | 34373 |
| 10 s | 503 | 29506 |
| 12 s | 483 | 34073 |
| 14 s | 434 | 35700 |
| 16 s | 281 | 26537 |

Figure 3:
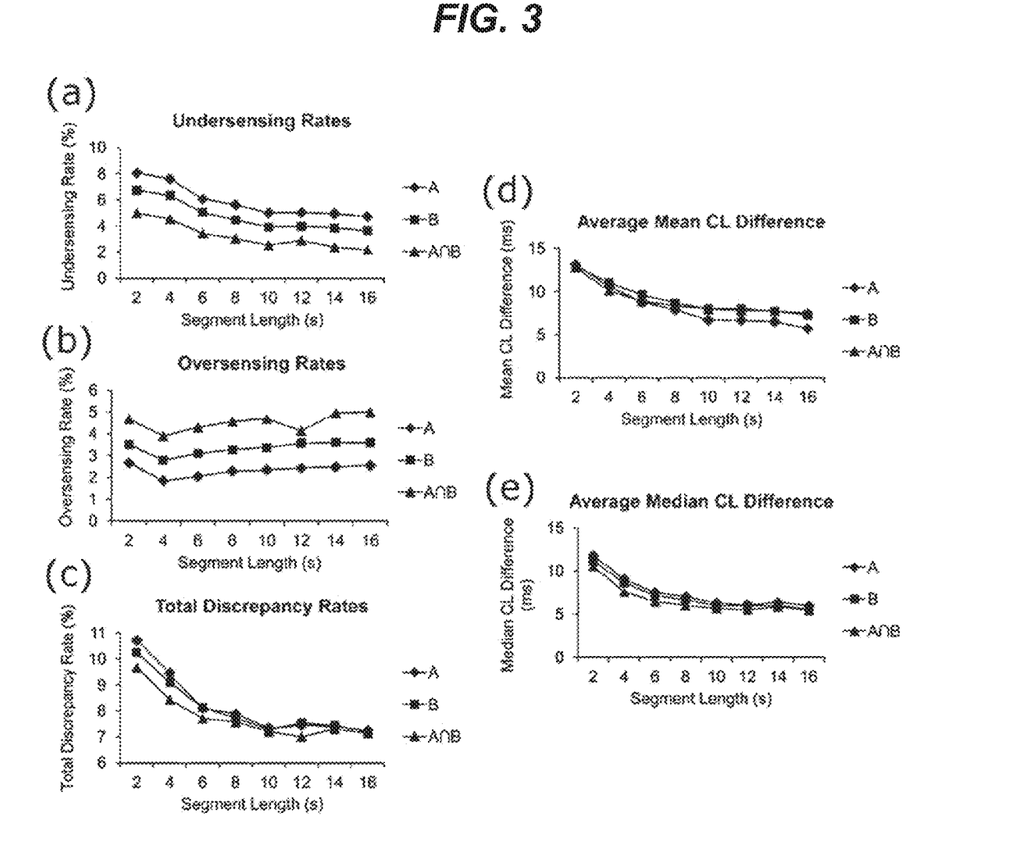
FIG. 3(a) shows the undersensing rate.
FIG. 3(b) shows the oversensing rates.
FIG. 3(c) shows the total discrepancy rates.
FIG. 3(d) shows the mean cycle length (CL) difference.
FIG. 3(e) shows that median cycle length difference.

FIGS. 3(a), 3(b), 3(c), 3(d), and 3(e) are graphical representations that illustrate the evaluation of the cycle length iteration algorithm against the manual markings from markers A and B and the intersection of the markings of A and B (A B) for different segment lengths. Specifically, FIG. 3(a) shows the undersensing rates, FIG. 3(b) shows the oversensing rates, FIG. 3(c) shows the total discrepancy rates, FIG. 3(d) shows the mean cycle length (CL) difference, and FIG. 3(e) shows that median cycle length difference.

The oversensing, undersensing and total discrepancy rates of the cycle length iteration algorithm compared to the two sets of manual markings and intersection of the manual markings for the different segment durations are shown in FIGS. 3(a)-3(c). The undersensing rate was highest when shorter segment durations were used. The oversensensing rate was more stable across the different segment durations. Marker A had higher undersensing rates than marker B. Marker B had higher oversensing rates than marker A. The intersection of A and B had lower undersensing rates and higher oversensing rates than either A or B. At 10 s durations, when the total discrepancy rate seem to stabilize, the undersensing, oversensing, and total discrepancy rates for the A and B intersection markings were 2.4%, and 7.0%, respectively.

Absolute differences in mean cycle length between the cycle length iteration algorithm and the manual markings are shown in FIG. 3(d). The absolute differences in median cycle length between the cycle length iteration and manual markings are shown in FIG. 3(e). Tracking with the undersensing rates, the absolute differences in cycle length are the highest with the shorter segment durations. At 10 s durations, the absolute differences in mean and median cycle lengths compared to the A and B intersection markings were 7.9±9.6 ms and 5.6±6.8 ms, respectively.

Figure 4:
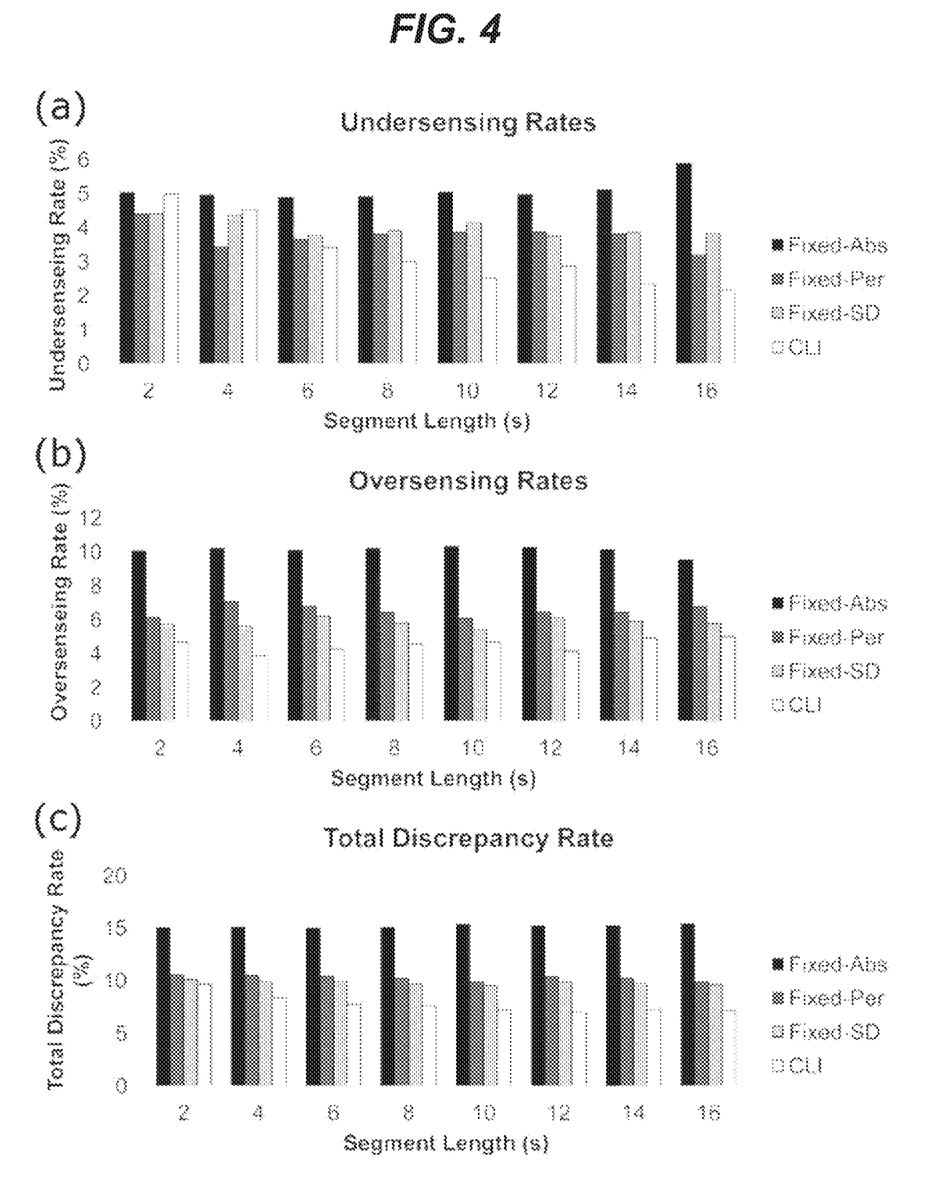
FIG. 4(a) shows comparisons of the undersensing rates.
FIG. 4(b) shows comparisons of the oversensing rates.
FIG. 4(c) shows comparisons of the total discrepancy rates with manual marking for the cycle length iteration algorithm and the fixed threshold algorithms, the comparisons including absolute amplitude (fixed-abs), percentage of maximum amplitude (fixed-per), and percentage of standard deviation (fixed-sd)

The results of a comparison of the undersensing, oversensing, and total discrepancy rates of the cycle length iteration algorithm relative to other activation detection methods are shown in FIGS. 4(a), 4(b), and 4(c), which are graphical representations, wherein FIG. 4(a) shows comparisons of the undersensing rates, FIG. 4(b) shows comparisons of the oversensing rates, and FIG. 4(c) shows comparisons of the total discrepancy rates with manual marking for the cycle length iteration algorithm and the fixed threshold algorithms. The comparisons include absolute amplitude (fixed-abs), percentage of maximum amplitude (fixed-per), and percentage of standard deviation (fixed-sd).

For this analysis, only the data using the intersection markings as the standard is presented. Fixed threshold detections were evaluated using the optimal thresholds that minimized the total discrepancy rates. The optimum absolute threshold values ranged from 8 to 9 μV depending on segment duration. The optimum threshold as a percentage of the maximum peak amplitude ranged from 5.5 to 9.5%. The optimum threshold as a percentage of one standard deviation ranged from 12 to 14%. Detection with the optimum raw threshold values had the highest discrepancy rates for all segment durations. The cycle length iteration algorithm had much lower oversensing rates than any of the fixed threshold methods and lower undersensing rates for segment lengths of 6 s or greater. Overall cycle length iteration had the lowest total discrepancy rates for all the segment lengths.

Figure 5:
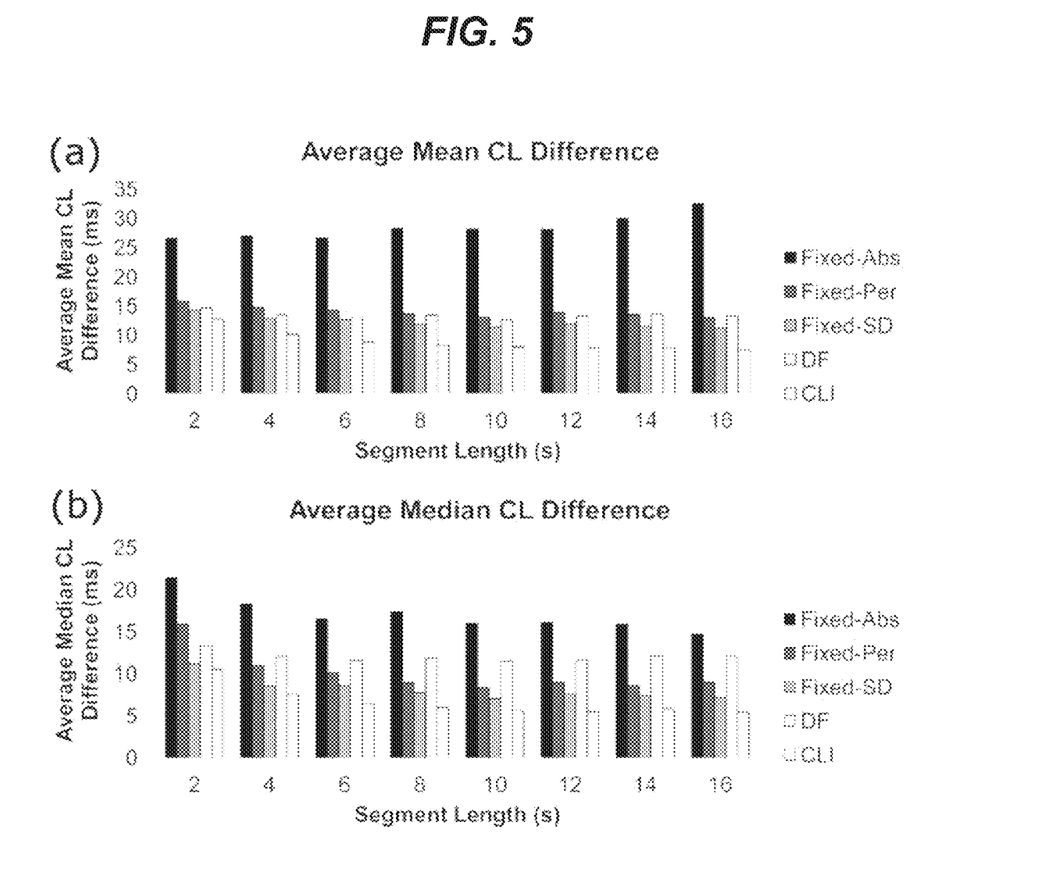
FIG. 5(a) shows comparisons of the mean cycle length (CL) difference.
FIG. 5(b) shows comparisons of the median cycle length difference with manual marking for the cycle length iteration algorithm, dominant frequency (DF) derived cycle length, and the fixed threshold algorithms, the comparisons including absolute amplitude (fixed-abs), percentage of maximum amplitude (fixed-per), and percentage of standard deviation (fixed-sd)

The absolute difference in mean and median cycle length of the automatic algorithms (including dominant frequency derived cycle length) with the manually marked intersection activations are shown in the graphical representations of FIGS. 5(a) and 5(b). FIG. 5(a) shows comparisons of the mean cycle length (CL) difference, and FIG. 5(b) shows comparisons of the median cycle length difference with manual marking for the cycle length iteration algorithm, dominant frequency (DF) derived cycle length, and the fixed threshold algorithms. The comparisons include absolute amplitude (fixed-abs), percentage of maximum amplitude (fixed-per), and percentage of standard deviation (fixed-sd).

Cycle length iteration had significantly lower absolute differences in both mean and median than the other algorithms for all segment lengths. For the 10 s segment length, the cycle length iteration absolute difference in mean cycle length (7.5±9.6 ms) was significantly less than that of dominant frequency (13.3±15.7 ms, $p<0.0001$), fixed absolute threshold (28.2±49.2 ms, $p<0.0001$), fixed percentage threshold (13.9±19.2 ms, $p<0.0001$), and fixed standard deviation threshold (11.5±15.1 ms, $p<0.0001$). The cycle length iteration absolute difference in median cycle length (5.4±7.2 ms) was also significantly less than that of dominant frequency (12.2±14.8 ms, $p<0.0001$), fixed absolute threshold (16.0±33.5 ms, $p<0.0001$), fixed percentage threshold (8.4±13.9 ms, $p<0.0001$), and fixed standard deviation threshold (7.1±10.1 ms, $p<0.0091$).

The inventive cycle length iteration algorithm was shown to detect atrial activations accurately from bipolar electrograms recorded during atrial fibrillation, and to provide cycle length estimations that more closely matched manually marked activations as compared to fixed threshold or dominant frequency-based methods. The criteria for mean and median cycle length convergence of this algorithm provides a detection criteria amidst the potentially very complex activation and morphology patterns of atrial fibrillation electrograms. Although this study evaluated the algorithm on electrograms in an offline setting, the algorithm is suitable for use in real-time applications.

Both time and frequency domain methods have previously been used to estimate local activation rates recording during atrial fibrillation. These cycle length measures have been shown to reflect the electrophysiological processes of atrial fibrillation, but the measures have not been adopted into routine clinical decision making. It is noteworthy that none of these prior methods has been robustly evaluated on large annotated datasets. Instead, the time and frequency domain methods have been evaluated against each other and it is unclear whether either of these approaches should be considered an adequate gold standard. In contrast, QRS detection algorithms can be tested using the several hours of annotated Holter electrocardiograms (ECGs) found in the MIT-BIH Physionet database. Note that "QRS" corresponds to the combination of three of the principal graphical deflections seen on a typical electrocardiogram (ECG), specifically the Q, R, and S waves.

The disclosure herein has employed manually marked electrograms as the basis for the evaluation of the cycle length iteration detection algorithm and comparison with dominant frequency and the fixed threshold algorithms. The manual marking of atrial fibrillation electrograms, however, is also not a straightforward process, as it sometimes requires subjective determinations of what is considered an activation. Electrograms during atrial fibrillation can have changing amplitudes and morphologies and can have very fractionated morphologies that make activation markings very difficult. Thus, the intersection set of markings from two independent reviewers is used that in theory would include the activations with the highest confidence. The cycle length iteration algorithm had the lowest percentage of combined undersensed and oversensed activations when the intersection set of manual markings was used as the reference.

Although the sensitivity and specificity of detecting atrial activations are important characteristics of the detection algorithm, the more critical evaluation criteria is the ability to estimate cycle length. When manually marking atrial fibrillation electrograms, a human is able to see the recording in its entirety. Mental notes of what the basic cycle length can be visually estimated and timing of where an activation should be can be made even though the deflections may be low amplitude in that spot. The iteration process of the cycle length iteration algorithm to detect activation until the mean and median cycle lengths converge more closely mimics the human detection process, whereas fixed threshold methods do not use the contextual information when detecting deflections. Thus, the cycle length iteration algorithm provides a very robust measurement of atrial fibrillation cycle length, especially if median cycle length is used.

There are some limitations to the cycle length iteration technique. First, there is a required stability during the recording segment in order for the algorithm to take advantage of mean and median cycle length convergence. Therefore, errors may occur if the cycle length iteration technique is used during phases of rapid change in atrial fibrillation cycle length that may occur with some interventions. Second, the cycle length iteration algorithm works significantly better with longer segment lengths, although the cycle length measurements at the short lengths were still better than those obtained using dominant frequency or fixed thresholds. Segment lengths of 10 s or more appear to provide optimal activation detection and cycle length estimation. Far field ventricular complexes are expected to remain as issues with the cycle length iteration algorithm, as they are with cycle lengths estimated with dominant frequency and fixed threshold techniques.

Mapping atrial fibrillation cycle lengths for the understanding of atrial fibrillation pathophysiology requires a certain amount of precision of the measurements to detect the subtle differences that exist with regions, interventions, and between subjects. Obtaining precise measurements is complicated by the complexity of atrial fibrillation electrograms. The cycle length iteration algorithm offers some improvement in this regard over other commonly used techniques, and can be used in either offline or real-time settings.

Figure 6:
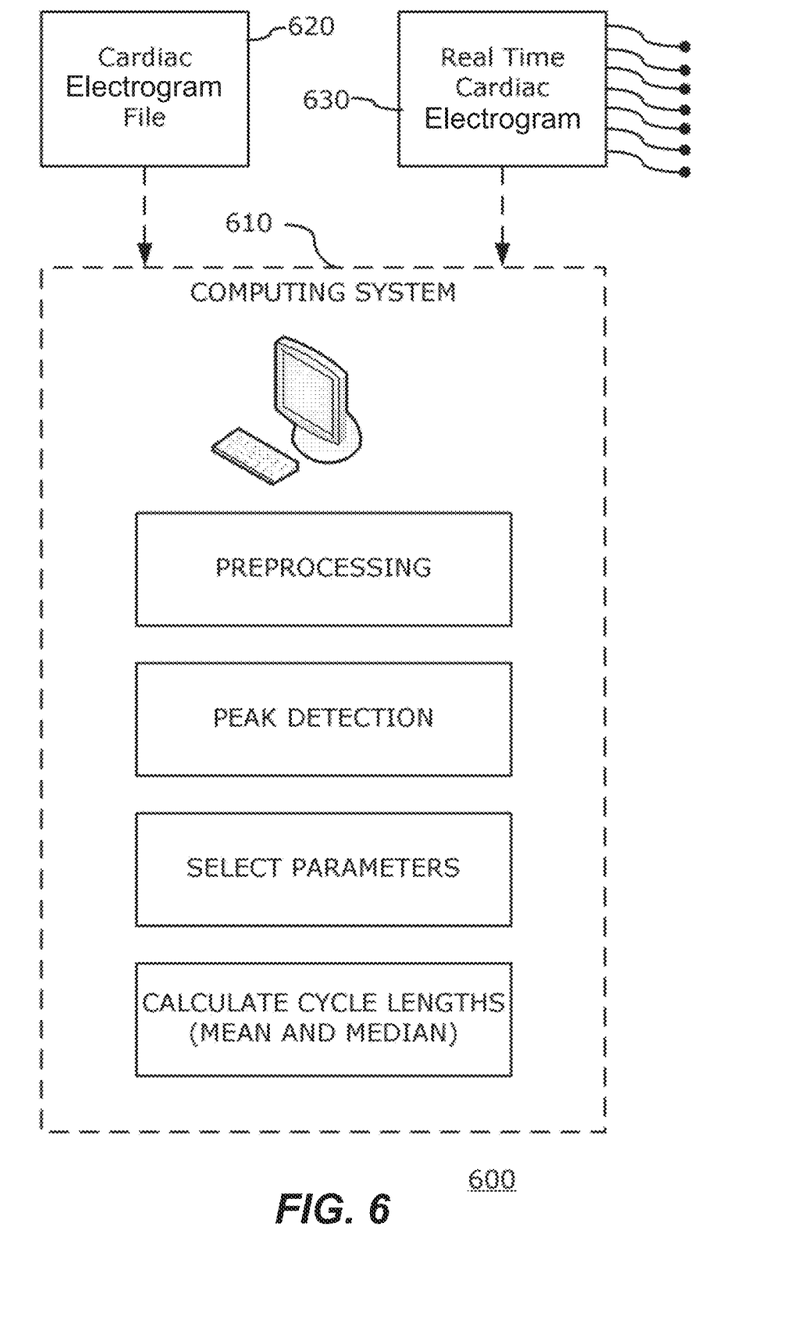
FIG. 6 is a simplified function block representation of a computer product implementation of the present disclosure.

FIG. 6 is a simplified function block representation of a computer product implementation 600 of the present disclosure. As shown in this figure, a computing system 610 receives a cardiac electrogram in either of two forms in this specific illustrative embodiment of the disclosure. The cardiac electrogram can be provided as a file 620 or as a real time cardiac electrogram 630.

As discussed above, computing system 610 takes, in this specific illustrative embodiment of the disclosure, the form of a computer that performs the functions of preprocessing the cardiac electrogram, detecting the peaks in the cardiac electrogram, and calculating the mean and median cycle lengths. This embodiment, however, enables the user (not shown) to select parameters using the computer keyboard, a mouse, a touch screen, or any other data input facility. Some of the parameters that can, in various embodiments of the disclosure be made selectable by the user include, for example, cardiac electrogram sample rate. noise blanking period length, segment length, minimum and maximum peak magnitudes, number of cycle lengths used to determine mean and median cycle lengths, maximum duration of the test, test duration as a function of difference between the mean and median cycle lengths, high pass filter frequency, low pass filter frequency, FFT parameters, minimum and maximum undersensing and/or oversensing rates, maximum and minimum discrepancy rates, etc.

Although the disclosure has been described in terms of specific embodiments and applications, persons skilled in the art can, in light of this teaching, generate additional embodiments without exceeding the scope or departing from the spirit of the claimed disclosure. Accordingly, it is to be understood that the drawing and description in this disclosure are proffered to facilitate comprehension of the disclosure, and should not be construed to limit the scope thereof. Moreover, the technical effects and technical problems in the specification are exemplary and are not limiting. The embodiments described in the specification may have other technical effects and can solve other technical problems.

I claim:

1. A system for analyzing a cardiac electrogram of an atrial fibrillation comprising:
   an electrogram device for taking, delivering, or storing a cardiac electrogram of an atrial fibrillation;
   a processor in electronic communication with the electrogram device;
   a memory in electronic communication with the processor, wherein the memory comprises programming code for execution by the processor, and the programming code is configured to: iteratively determine cycle lengths between activation peaks of the cardiac electrogram of the atrial fibrillation, applying iteratively adjusted detection threshold levels, until a mean of the determined cycle lengths meets at least one criteria; and determine an atrial fibrillation cycle length of the atrial fibrillation when the mean of the determined cycle lengths meets the at least one criteria; and
   a device for treating a site of atrial fibrillation sources based on the determined atrial fibrillation cycle length.

2. The system of claim 1 wherein the programming code is configured to determine whether the mean of the determined cycle lengths is less than a predetermined time.

3. The system of claim 1 wherein the programming code is configured to determine whether the mean of the determined cycle lengths is within a predetermined range of a median of the determined cycle lengths.

4. The system of claim 1 wherein the programming code is configured to determine whether an amplitude of one of the activation peaks is outside a predetermined range of the amplitude of a preceding activation peak.

5. The system of claim 1 wherein the programming code is configured to determine whether any of the determined cycle lengths are outside a predetermined range of a median of the determined cycle lengths.

6. The system of claim 1 wherein the programming code is configured to determine times and amplitudes of the highest activation peaks; remove all peaks within a predetermined time range of each of the highest activating peaks; and determine successive cycle lengths between chronologically sorted times of the highest activation peaks.

7. The system of claim 1 wherein the programming code is configured to iteratively determine the cycle lengths between the activation peaks of the cardiac electrogram of the atrial fibrillation, applying the iteratively adjusted detection threshold levels, until: the mean of the determined cycle lengths is less than a predetermined time; the mean of the determined cycle lengths is within a predetermined range of a median of the determined cycle lengths, or an amplitude of one of the activation peaks is outside a predetermined range of the amplitude of a preceding activation peak; and none of the determined cycle lengths are outside a predetermined range of a median of the determined cycle lengths.

8. The system of claim 1 wherein the programming code is configured to preprocess the cardiac electrogram of the atrial fibrillation.

9. The system of claim 8 wherein the preprocessing comprises subjecting the cardiac electrogram of the atrial fibrillation to filtering and rectifying.

10. The system of claim 1 wherein the device for treating the site of the atrial fibrillation sources comprises an ablation device for ablating the site of the atrial fibrillation sources.

11. The system of claim 1 wherein the device for treating the site of the atrial fibrillation sources comprises a diagnostic device for mapping the site of the atrial fibrillation sources.

* * * * *